United States Patent
Kim et al.

(10) Patent No.: US 11,698,385 B2
(45) Date of Patent: Jul. 11, 2023

(54) WALKING INTENSITY DETECTION AND TRENDING IN A WEARABLE CARDIOVERTER DEFIBRILLATOR

(71) Applicant: West Affum Holdings Corp., Grand Caymen (KY)

(72) Inventors: Jaeho Kim, Redmond, WA (US); Pamela F. Breske, Newcastle, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 0 days.

(21) Appl. No.: 17/378,421

(22) Filed: Jul. 16, 2021

(65) Prior Publication Data
US 2022/0146547 A1    May 12, 2022

Related U.S. Application Data

(60) Provisional application No. 63/112,225, filed on Nov. 11, 2020.

(51) Int. Cl.
*G01P 13/00*    (2006.01)
*G01P 15/18*    (2013.01)
*G01C 22/00*    (2006.01)
*A61N 1/39*    (2006.01)

(52) U.S. Cl.
CPC ............ *G01P 13/00* (2013.01); *G01C 22/006* (2013.01); *G01P 15/18* (2013.01); *A61N 1/3904* (2017.08)

(58) Field of Classification Search
None
See application file for complete search history.

(56) References Cited

U.S. PATENT DOCUMENTS

| | | |
|---|---|---|
| 3,724,455 A | 4/1973 | Unger |
| 4,583,524 A | 4/1986 | Hutchins |
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |

(Continued)

FOREIGN PATENT DOCUMENTS

| | | |
|---|---|---|
| EP | 3380189 B1 | 10/2018 |
| WO | 1998039061 A2 | 9/1998 |
| WO | 2012064604 A1 | 5/2012 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Raul J Rios Russo
*Assistant Examiner* — Carl F. R. Tchatchouang
(74) *Attorney, Agent, or Firm* — Columbia IP Law (57) ABSTRACT

Technologies and implementations for a wearable healthcare system, which may be worn by a person. The wearable healthcare systems may include one or more motion sensors. A motion analysis modules may be included in the wearable healthcare system, which may be configured to determine physical activities and intensity of the physical activities of the person.

23 Claims, 8 Drawing Sheets

(56) References Cited

U.S. PATENT DOCUMENTS

| | | | |
|---|---|---|---|
| 5,348,008 A | 9/1994 | Bornn et al. | |
| 5,353,793 A | 10/1994 | Bornn | |
| RE34,800 E | 11/1994 | Hutchins | |
| 5,394,892 A | 3/1995 | Kenny | |
| 5,405,362 A | 4/1995 | Kramer et al. | |
| 5,474,574 A | 12/1995 | Payne et al. | |
| 5,618,208 A | 4/1997 | Crouse et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 5,944,669 A | 8/1999 | Kaib | |
| 6,047,203 A | 4/2000 | Sackner et al. | |
| 6,065,154 A | 5/2000 | Hulings et al. | |
| 6,108,197 A | 8/2000 | Janik | |
| 6,148,233 A | 11/2000 | Owen et al. | |
| 6,201,992 B1 | 3/2001 | Freeman | |
| 6,263,238 B1 | 7/2001 | Brewer et al. | |
| 6,287,328 B1 | 9/2001 | Snyder et al. | |
| 6,304,780 B1 | 10/2001 | Owen et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,427,083 B1 | 7/2002 | Owen et al. | |
| 6,437,083 B1 | 7/2002 | Owen et al. | |
| 6,529,875 B1 | 3/2003 | Nakajima | |
| 6,546,285 B1 | 4/2003 | Owen et al. | |
| 6,671,545 B2 | 12/2003 | Fincke | |
| 6,681,003 B2 | 1/2004 | Linder et al. | |
| 6,762,917 B1 | 7/2004 | Verbiest et al. | |
| 7,065,401 B2 | 6/2006 | Worden | |
| 7,559,902 B2 | 7/2009 | Ting et al. | |
| 7,865,238 B2 | 1/2011 | Brink | |
| 7,870,761 B2 | 1/2011 | Valentine et al. | |
| 7,974,689 B2 | 7/2011 | Volpe et al. | |
| 8,135,462 B2 | 3/2012 | Owen et al. | |
| 8,140,154 B2 | 3/2012 | Donnelly et al. | |
| 8,369,944 B2 | 2/2013 | Macho et al. | |
| 8,548,557 B2 | 10/2013 | Garstka et al. | |
| 8,615,295 B2 | 12/2013 | Savage et al. | |
| 8,644,925 B2 | 2/2014 | Volpe et al. | |
| 8,676,313 B2 | 3/2014 | Volpe et al. | |
| 8,897,860 B2 | 11/2014 | Volpe et al. | |
| 8,904,214 B2 | 12/2014 | Volpe et al. | |
| 8,965,500 B2 | 2/2015 | Macho et al. | |
| 9,008,801 B2 | 4/2015 | Kaib et al. | |
| 9,089,685 B2 | 7/2015 | Sullivan et al. | |
| 9,131,901 B2 | 9/2015 | Volpe et al. | |
| 9,132,267 B2 | 9/2015 | Kaib | |
| 9,408,548 B2 | 8/2016 | Volpe et al. | |
| 9,454,219 B2 | 9/2016 | Volpe et al. | |
| 9,592,403 B2 * | 3/2017 | Sullivan | A61N 1/3925 |
| 9,878,171 B2 | 1/2018 | Kaib | |
| 2003/0158593 A1 | 8/2003 | Heilman et al. | |
| 2005/0107833 A1 | 5/2005 | Freeman et al. | |
| 2005/0107834 A1 | 5/2005 | Freeman et al. | |
| 2006/0173499 A1 | 8/2006 | Hampton et al. | |
| 2008/0312709 A1 | 12/2008 | Volpe et al. | |
| 2009/0005827 A1 | 1/2009 | Weintraub et al. | |
| 2010/0007413 A1 | 1/2010 | Herleikson | |
| 2010/0298899 A1 | 11/2010 | Donnelly et al. | |
| 2011/0022105 A9 | 1/2011 | Owen et al. | |
| 2011/0257496 A1 * | 10/2011 | Terashima | A61B 5/74 600/347 |
| 2011/0288604 A1 | 11/2011 | Kaib et al. | |
| 2011/0288605 A1 | 11/2011 | Kaib et al. | |
| 2012/0112903 A1 | 5/2012 | Kaib et al. | |
| 2012/0144551 A1 | 6/2012 | Guldalian | |
| 2012/0150008 A1 | 6/2012 | Kaib et al. | |
| 2012/0158075 A1 | 6/2012 | Kaib et al. | |
| 2012/0265265 A1 | 10/2012 | Razavi et al. | |
| 2012/0283794 A1 | 11/2012 | Kaib et al. | |
| 2012/0293323 A1 | 11/2012 | Kaib et al. | |
| 2012/0302860 A1 | 11/2012 | Volpe et al. | |
| 2012/0310315 A1 | 12/2012 | Savage et al. | |
| 2013/0085538 A1 | 4/2013 | Volpe et al. | |
| 2013/0231711 A1 | 9/2013 | Kaib | |
| 2013/0245388 A1 | 9/2013 | Rafferty et al. | |
| 2013/0274565 A1 | 10/2013 | Langer et al. | |
| 2013/0317852 A1 | 11/2013 | Worrell et al. | |
| 2013/0325078 A1 | 12/2013 | Whiting et al. | |
| 2014/0012144 A1 | 1/2014 | Crone | |
| 2014/0025131 A1 | 1/2014 | Sullivan et al. | |
| 2014/0046391 A1 | 2/2014 | Cowan et al. | |
| 2014/0070957 A1 | 3/2014 | Longinotti-Buitoni et al. | |
| 2014/0163663 A1 | 6/2014 | Poddar et al. | |
| 2014/0278139 A1 * | 9/2014 | Hong | G01C 22/006 702/19 |
| 2014/0324112 A1 | 10/2014 | Macho et al. | |
| 2014/0378812 A1 | 12/2014 | Saroka et al. | |
| 2015/0039053 A1 | 2/2015 | Kaib et al. | |
| 2015/0328472 A1 | 11/2015 | Sullivan et al. | |
| 2016/0004831 A1 | 1/2016 | Carlson et al. | |
| 2016/0082277 A1 | 3/2016 | Foshee, Jr. et al. | |
| 2019/0209853 A1 * | 7/2019 | Kim | A61N 1/3987 |

OTHER PUBLICATIONS

LIFECOR LifeVest System Model WCD 3100 Operator's Manual, 2006, PN 20B0040 Rev Fl, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C. Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

WALKING INTENSITY DETECTION AND TRENDING IN A WEARABLE CARDIOVERTER DEFIBRILLATOR

RELATED APPLICATION

This application claims benefit of priority to U.S. Provisional Patent Application Ser. No. 63/112,225, filed on Nov. 11, 2020, titled WALKING INTENSITY DETECTION AND TRENDING IN A WEARABLE CARDIOVERTER DEFIBRILLATOR, which is incorporated herein by reference in its entirety for all purposes.

INFORMATION

Unless otherwise indicated herein, the approaches described in this section are not prior art to the claims in this application and are not admitted to be prior art by inclusion in this section.

Technology has contributed to improvements in healthcare. Some examples include healthcare related devices that may be mobile and personal. Mobile and personal healthcare devices may include Wearable Medical Devices (WMDs). Some WMDs may include medical devices that facilitate monitoring and treatment of various health related activities of a person. For example, a WMD may include a medical device that may be used to monitor a person's heart activity, including treatment of the heart. The heart activity monitored by the WMD may be in the form of electrical signals (i.e., electrocardiogram or ECG). Treatment of the heart may be in the form of a defibrillating shock, which may be administered responsive to the monitoring detecting a condition to trigger the treatment.

A WMD may be in a mobile form factor such as, but not limited to, a wearable support structure capable of being worn by a person, whose heart activity is to be monitored and/or treated. Having the WMD in a mobile form factor may facilitate continuous monitoring of a person's ECG, which may facilitate detection of heart related issues, including treatment of the heart related issues. Additionally, having the WMD in the mobile form factor wearable by the person may facilitate tracking of physical activities of the person wearing the WMD (e.g., steps).

An example of a WMD in a mobile form factor, which may be used to monitor and facilitate therapy of a person's heart activity, may be a wearable cardioverter defibrillator (WCD). Some examples of WCDs may include various components to facilitate monitoring and treatment of the person's heart such as, but not limited to, electrodes. Some of the electrodes may be configured to monitor the person's heart activity (e.g., electrocardiogram or ECG electrodes). Some of the electrodes may be configured to facilitate providing an electrical shock to the person as treatment (e.g., therapy treatment electrodes). As part of the health related components of the WCD (e.g., monitoring and treatment of the person's heart), the WCD may include components to detect and/or determine physical activities of the person wearing the WCD (e.g., motion detection). However, detecting motion alone may not facilitate determination of the person's overall health.

All subject matter discussed in this section of this document is not necessarily prior art and may not be presumed to be prior art simply because it is presented in this section. Plus, any reference to any prior art in this description is not and should not be taken as an acknowledgement or any form of suggestion that such prior art forms parts of the common general knowledge in any art in any country. Along these lines, any recognition of problems in the prior art are discussed in this section or associated with such subject matter should not be treated as prior art, unless expressly stated to be prior art. Rather, the discussion of any subject matter in this section should be treated as part of the approach taken towards the particular problem by the inventor(s). This approach in and of itself may also be inventive. Accordingly, the foregoing summary is illustrative only and not intended to be in any way limiting. In addition to the illustrative aspects, embodiments, and features described above, further aspects, embodiments, and features will become apparent by reference to the drawings and the following detailed description.

SUMMARY

Described herein are various illustrative wearable healthcare systems, which may be worn by a person. Example wearable healthcare systems may include one or more motion sensors. Some example wearable healthcare systems may include motion analysis modules configured to determine physical activities and intensity of the physical activities. Additionally, some example wearable healthcare systems may include motion analysis modules configured to determine trends in intensity of the physical activity, which may be an indication of one or more wellness parameters of the person. Further, example wearable healthcare systems may include motion analysis modules configured determine a pattern of the physical activity of the person. The determined pattern may be utilized to determine one or more wellness parameters of the person.

Some example wearable healthcare systems may include motion analysis modules configured to determine recommend physical activities based, at least in part, on the determined trends and/or patterns. The recommendation may be to address the one or more wellness parameters of the person.

The foregoing summary is illustrative only and not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings.

DETAILED DESCRIPTION

The following description sets forth various examples along with specific details to provide a thorough understanding of claimed subject matter. It will be understood by those skilled in the art after review and understanding of the present disclosure, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to apparatus and systems related to a wearable medical device (WMD) having one or more motion sensors to detect motion and orientation of the WMD worn by a person to facilitate determination of one or more wellness parameter of the person. The determination of the wellness parameter of the person may be facilitated further by detecting a motion intensity (e.g., walking intensity or walking cadence), which may include intensity and trend information. Some of the determined wellness parameter may facilitate determining a recommendation of an activity level to improve the wellness parameter. Accordingly, the WMD having one or more motion sensors may facilitate improved wellness of a person.

In the present disclosure, a WMD may include a medical device that may be configured to facilitate monitoring and treatment of potential issues with a person's heart (i.e., the person may have a health condition, where the electrical control system of the heart may malfunction causing the heart to beat irregularly or not at all). Commonly, these types of medical devices may include a defibrillator device (e.g., a wearable cardioverter defibrillator or WCD). In the present disclosure, the WCD may include one or more motion sensors. Accordingly, the disclosure will be described referencing medical devices having one or more motion sensors, in accordance with various embodiments.

Briefly, the above mentioned issue with the rate of the heartbeat may be generally referred to as arrhythmia. Arrhythmia may be caused by many factors, but in general, arrhythmia may be caused by a malfunction in the electrical control system of the heart. Some types of arrhythmias may result in inadequate blood flow resulting in reduction or lack of the amount of blood pumped to the various parts of the body. For example, issues with the sinoatrial (SA) node may lead to arrhythmia of some kind. Some arrhythmias may lead to a condition known as sudden cardiac arrest (SCA). In an SCA condition, the heart may fail to pump blood effectively, and as a result, death may occur.

An example type of arrhythmia, which may be associated with SCA, may be a condition known as ventricular fibrillation (VF). VF may be a condition where a ventricle or ventricles, which make up the heart to facilitate the pumping of blood, may make uncoordinated movements instead of steady rhythmic movements. In the VF condition, the heart may not pump adequate amounts of blood or may not pump blood at all, which may eventually lead to death. Another type of arrhythmia, which may be associated with SCA, may be a condition known as ventricular tachycardia (VT).

Turning back to the medical device configured to be utilized to help treat VF by defibrillating the heart, the medical device may be capable of monitoring the electrical signals of the person's heart, and if necessary, administer therapy to the heart in the form of an electric shock. The medical device may monitor the electrical signals and provide the electric shock to the heart externally (i.e., through the surface of a body) via components commonly known as electrodes. The medical device may be in the form of a cardioverter defibrillator. The medical device may be included in a support structure configured to be worn by the person. In this example, the medical device may help facilitate monitoring the electrical activities of the person's heart and providing the electric shock to the heart in the VF condition. As a result, the medical device may help prevent Sudden Cardiac Death (SCD).

In some embodiments, the medical device may include one or more motion sensors to detect motion and orientation of the WMD worn by a person facilitating determination of a wellness of the person. For example, the medical device may include motion sensors implemented utilizing one or more accelerometers such as, but not limited to, the implementations disclosed in US Pat. App. Pub. No. US20190209853A1, filed on Oct. 11, 2018, titled "DETECTING WALKING IN A WEARABLE CARDIO-VERTER DEFIBRILLATOR SYSTEM" ("853 app"), which is incorporated by reference in its entirety for all purposes.

Before to turning the figures, a non-limiting example scenario may be described. In the non-limiting example scenario, a person may have a heart condition, where the person may utilize a wearable medical device (WMD). The WMD may be configured to facilitate monitoring and treatment of the person's heart condition such as, but not limited to, a wearable cardioverter defibrillator (WCD). In one example, the WCD may include one or more motion sensors. The motion sensors may include accelerometers such as, but not limited to, those disclosed in the above referenced patent application, where the WCD may help facilitate detection of motion and orientation. In accordance with various embodiments disclosed herein, the WCD may be configured to determine a wellness of a person based, at least in part, on the detected motion and orientation.

In the non-limiting scenario, the person may be wearing the WCD. As the person moves, the one or more motion sensors included in the WCD may detect the movement, including the orientation of the movement. The detected movement may be the person engaged in some physical activity such as, but not limited to, walking. As the person walks, the WCD may be configured to receive the data from the one or more sensors to determine various information regarding the walk such as, but not limited to, a count of the steps, including the number of steps on a periodic basis (i.e., pace or cadence), direction of the walk, elevation changes during the walk (e.g., climbing hills or climbing steps), and so forth. From the pace or cadence of the walk, an intensity of the walk may be determined. The intensity of the walk may be received over time for the WCD to determine a trend in the intensity of the physical activity (e.g., walking), in turn, the trend in the intensity may be utilized by the WCD to determine one or more wellness parameters of the person.

Continuing with the non-limiting scenario, in one example, the person may walk at a slower pace over a period of time (e.g., during a week). The WCD may determine that the trend in the intensity of the walk may be decreasing. The decreasing trend may be an indication of a health issue of the person. For example, the person may be experiencing an increase in labored breathing, physical pain (e.g., joint or muscle pain), fatigue, and/or so forth. That is, the decrease in the trend of the intensity of the walk may be indicative of the one or more wellness parameters of the person trending or heading to an undesirable direction. The information regarding the one or more wellness parameters may be communicated to the person and/or to healthcare personnel by the WCD. Responsive to the negative changes in the one or more wellness parameters, the WCD may utilize the various information regarding the physical activity, including intensity, to determine a recommended activity or activity level for the person to help address the negative changes in the one or more wellness parameters. The recommended activity may be communicated to the person and/or to healthcare personnel. This recommendation may be in addition to the WCD being configured to set one or more initial goals for the person (e.g., number of total steps for a period of time, a pace or cadence of the walk, a trend of increasing for a period of time, etc.). The WCD may be configured to commend the person for meeting and/or exceeding the one or more goals, including encouraging the person to meet the various goals.

In another example, the person may walk at a faster pace over a period of time (e.g., during a week). The WCD may determine that the trend in the intensity of the walk may be increasing. The increasing trend may be an indication of an improvement of the health of the person. For example, the person may be increasing in strength to be able to walk at an increasing pace and/or cadence (i.e., walk faster). In this example, the WCD may be configured to set one or more goals for the person (e.g., number of total steps for a period of time, a pace or cadence of the walk, a trend of increasing for a period of time, etc.). Because the trend in intensity may be increasing, the WCD may be configured to commend the person for meeting and/or exceeding the one or more goals, including encouraging the person to meet the various goals.

Continuing with the non-limiting scenario, a pattern of the person's activity (e.g., the walk) may be determined. The determined pattern may help measure one or more wellness parameters of the person similar to the intensity pattern as described above. The pattern of the walk may include a wide variety of patterns such as, but not limited to, how often the person walks during a period of time (e.g., per day, per week, per month, etc.), how long the person walks (e.g., 30 minutes, 1 hour, etc.), time of day that the person walks, intensity of the walks, and so forth. These patterns may be utilized to measure one or more wellness parameter of the person.

In one example, if the determined pattern indicates less activity for a period of time (e.g., the person is walking less per day or per week), the WCD may be configured to provide an indication of the change and/or trend in the wellness parameter of the person because there may be a change in the health of the person resulting in less activity (e.g., injury, unwell, etc.). The indication of the change and/or trend in the wellness parameter may be communicated to the person via an interface and/or transmitted to a healthcare provider. In some cases, the indication may be transmitted to emergency personnel (e.g., serious illness, which may be causing the change).

In another example, if the determined pattern indicates more activity for a period of time (e.g., the person is walking more per day or per week), the WCD may be configured to provide an indication of the change and/or trend in the one or more wellness parameters of the person because there may be a change in the health of the person resulting in more activity (e.g., increased strength, stamina, weight loss, etc.).

In the examples of the determination of the patterns above, the WCD may be configured to set various goals and/or provide recommendations. Additionally, as described above with respect to determined trends in intensity, the WCD may be configured to commend the person for meeting various goals, including encouraging the person to meet the various goals.

Figure 1:
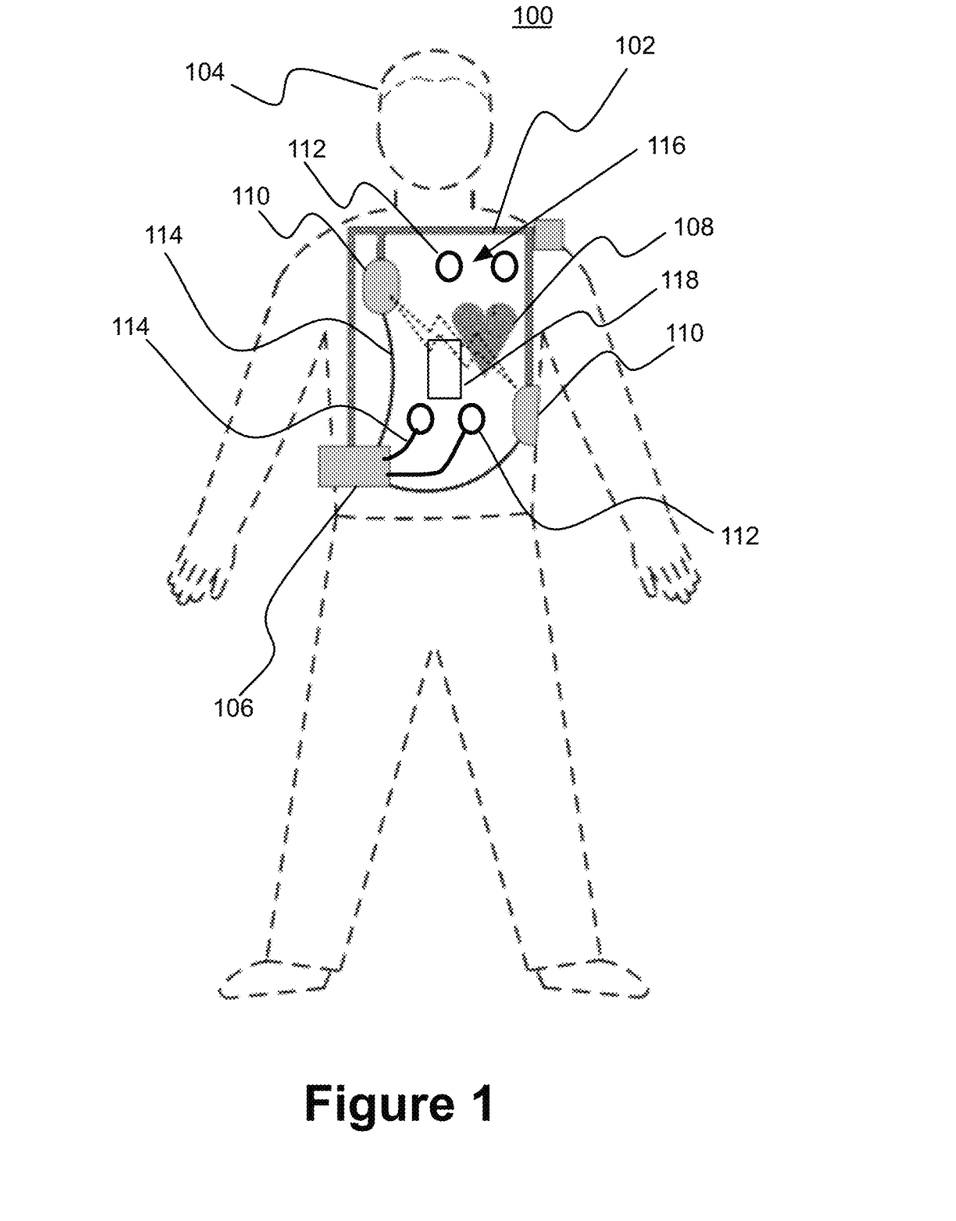
FIG. 1 illustrates a wearable cardioverter defibrillator (WCD), in accordance with various embodiments.

Turning now to FIG. 1, FIG. 1 illustrates a wearable medical device (WMD), in accordance with various embodiments. In FIG. 1, a WMD may be configured to facilitate monitoring and treatment of a person's heart such as, but not limited to, a wearable cardioverter defibrillator (WCD) 100. The WCD 100 may be included in a support structure 102, which may be configured to be worn by a person 104. The WCD 100 may include various electronic components to facilitate the functionality of the WCD 100 as a heart monitoring and defibrillator device. The various electronic components may be illustrated as a WCD module (hereon a WCD monitor 106). The WCD 100 may include two therapy electrodes configured to defibrillate a person's heart 108, defibrillator electrodes 110, and a number of monitoring electrodes 112 configured to detect and measure the person's electrical heart activity (e.g., electrocardiogram or ECG). As shown, the monitoring electrodes 112 and the defibrillator electrodes 110 may be located proximate to the person's heart 108 and chest area 116. The monitoring electrodes 112 and the defibrillator electrodes 110 may be communicatively coupled to the WCD monitor 106 via a number of electrical leads 114. Additionally, shown in FIG. 1, the support structure may be configured to facilitate inclusion of one or more motion sensors (hereon, motion sensor 118). The motion sensor 118 may be communicatively coupled to the WCD monitor 106 via wired or wireless communication methodologies.

As described herein, the motion sensor 118, included in the support structure 102, may be configured to detect motion in accordance with various embodiments. Examples of a motion sensor may include accelerometers, where the accelerometers may be configured to measure acceleration and/or orientation relative to gravity along 3 orthogonal axes. Some additional examples of a motion sensor may include 9-axis absolute orientation sensor, which may have a combination of 3-axis acceleration sensor, a 3-axis gyroscope, and a 3-axis geomagnetic sensor. A 9-axis absolute orientation sensor may be of the kind available from Bosch Sensortec GmbH of Reutlingen, Germany. In addition to the various axis related sensors, some other example motion sensor may include global positioning system (GPS) components and/or barometer components. Further, the motion sensor 118 may include force, pressure, inertial, velocity, and position sensors such as, but not limited to, those sensors available from Sensoria, Inc., of Redmond, Wash. Accordingly, the claimed subject matter is not limited in this respect.

In FIG. 1, when the person 104 moves while wearing the WCD 100, the motion sensor 118 may detect the motion and transmit the signal to the WCD monitor 106 to be processed. As will be described in more detail with respect to FIG. 8, the WCD monitor 106 may include various electronic components, including one or more processors, configured to implement the various examples claimed and disclosed herein.

Figure 2:
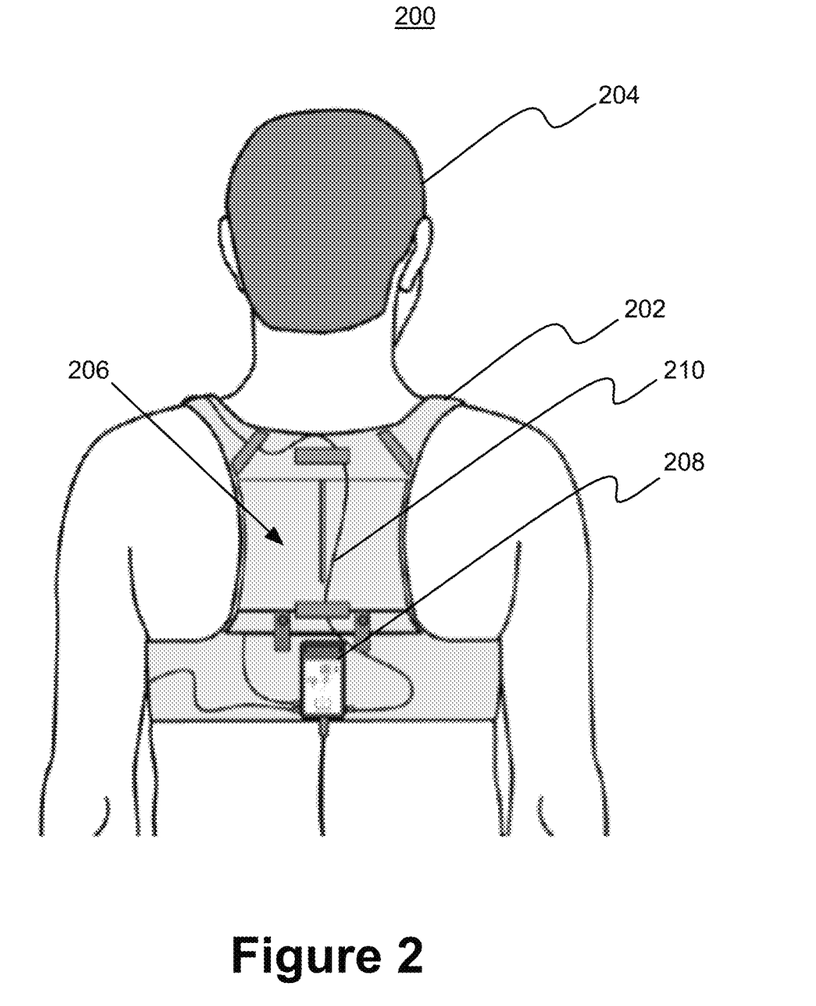
FIG. 2 illustrates a back view of a WCD, in accordance with various embodiments.

FIG. 2 illustrates a back view of a WCD, in accordance with various embodiments. In FIG. 2, a WCD 200 may be configured to be included in a support structure 202 configured to be worn by a person 204. The support structure 202 may have a back side 206. The back side 206 may be configured to accommodate a motion sensor 208. Additionally, shown in FIG. 2, one or more electrical leads 210 may be included in the support structure 202 to facilitate communicatively coupling the motion sensor 208 with a WCD monitor (e.g., shown in FIG. 1). As will be describe in more detail, as the person 204 moves (e.g., walk), the motion sensor 208 may detect the motion including intensity. The detected motion sensor 208 may be communicated to the WCD to be processed in accordance with various embodiments.

In FIG. 2, even though the motion sensor 208 may be shown as being proximately located at the back side 206 of the person 204, the location of the motion sensor 208 may be a variety of locations such as, but not limited to a front side, left or right side, and so forth. Additionally, the motion sensor 208 may be located separately from a WCD monitor (e.g., WCD monitor 106 shown in FIG. 1). However, in some embodiments, the motion sensor 208 may be included in a WCD monitor and may be a component of a WCD monitor. Accordingly, the claimed subject matter is not limited in this respect.

Figure 3:
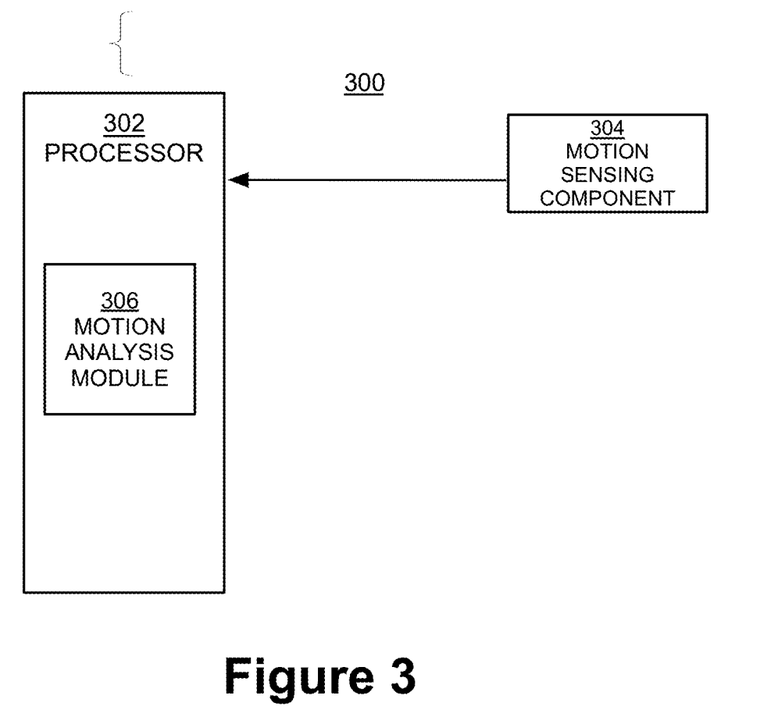
FIG. 3 illustrates a block diagram of a system for detecting motion and intensity of physical activity of a person, in accordance with various embodiments.

FIG. 3 illustrates a block diagram of a system for detecting motion and intensity of physical activity of a person, in accordance with various embodiments. In FIG. 3, a system 300 may include a processor 302 and a motion sensing component (hereon, motion sensor 304) communicatively coupled to the processor 302. Additionally, the processor 302 may include a motion analysis module (hereon, motion module 306). The motion sensor 304 may include one or more motion sensors such as, but not limited to, the 3-axis accelerometer described above. The motion module 306 may be configured to facilitate the processor 302 to determine the various motion related information as described herein. As will be described in detail with respect to FIG. 8, the system 300 may be included in a WCD. Additionally, the system 300 may be separate components communicatively coupled with a WCD. Accordingly, the motion sensor 304 may be included in a WCD or located separately, while being communicatively coupled with a WCD. The claimed subject matter is not limited in this respect.

In FIG. 3, when a person wearing a WCD such as those illustrated in FIG. 1 and FIG. 2, the motion sensor 304 may be configured to detect motion. When the person wearing the WCD moves to engage in some physical activity, the motion sensor 304 may communicate the detected motion to the processor 302. The motion module 306 may be configured to facilitate, by the processor 302, analysis of the received detected motion from the motion sensor 304. As described in the above non-limiting scenario, in one example, the motion module 306 may facilitate determination of an intensity of the physical activity. The intensity of the physical activity may be received over time by the processor 302, and the motion module 306 may facilitate determination of a trend in the intensity of the physical activity. The motion module 306 may be configured to facilitate analysis of the trend in the intensity of the physical activity may be analyzed by the motion module 306, which may be utilized to determine one or more wellness parameters of the person.

In another example, the motion module 306 may be configured to facilitate determination of a pattern of the physical activity. The determined pattern of the physical activity may help measure one or more wellness parameters of the person similar to the intensity pattern. The pattern of the physical activity may include a wide variety of patterns such as, but not limited to, how often the person engages in physical activity during a period of time (e.g., per day, per week, per month, etc.), how long the person engages in physical activity (e.g., 30 minutes, 1 hour, etc.), time of day that the person engages in physical activity, intensity of the physical activity, and so forth. These patterns may be utilized to measure one or more wellness parameter of the person.

Some examples of detection of physical activities such as, but not limited to, walking, may be illustrated in the methodologies disclosed in aforementioned 853 app. The claimed subject matter disclosed in the present application may utilize the methodologies disclosed in the 853 app.

Figure 4:
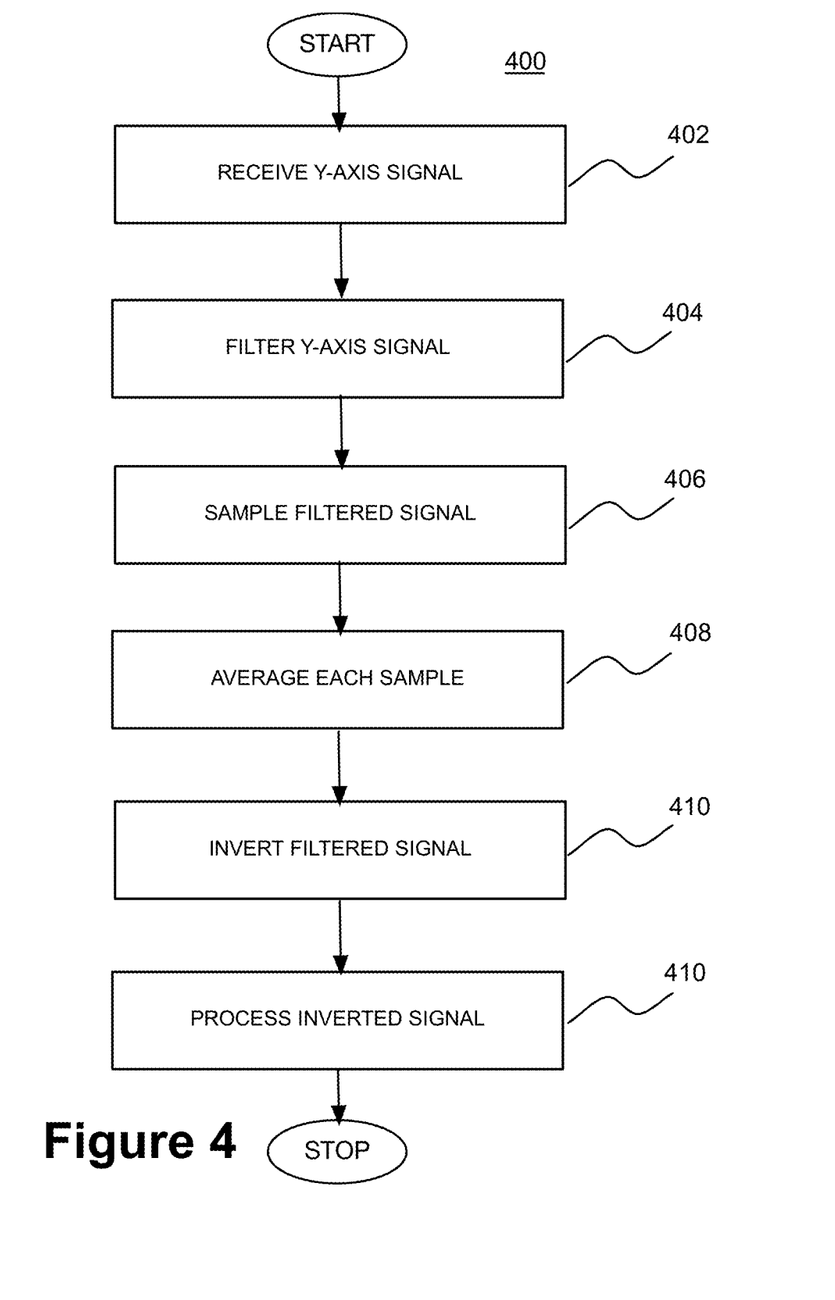
FIG. 4 illustrates an operational flow for detection of physical activity and its intensity, in accordance with at least some embodiments described herein.

FIG. 4 illustrates an operational flow for detection of physical activity and its intensity, in accordance with at least some embodiments described herein. In some portions of the descriptions, illustrative implementations of the method may be described with reference to a WCD depicted in FIGS. 1 and 2 and system for detecting motion and intensity of physical activity depicted in FIG. 3. Additionally, the methods and implementation of the method may utilize the methodologies described in the 853 app for detection of physical activity.

Additionally, FIG. 4 employs block diagrams to illustrate the example methods detailed therein. These block diagrams may set out various functional blocks or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in the figures may be eliminated. In some examples, the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of claimed subject matter.

In some examples, operational flow 400 may be employed as part of motion module 306 (shown in FIG. 3). Beginning at block 402 ("Receive Y-axis Signal"), the motion module 306 may receive y-axis accelerometer signal from detection of motion from the one or more motion sensors. That is, the Y-axis may represent the person's up and down acceleration (e.g., when the person stands or sits straight up). For the example operational flow 400, the physical activity detected and analyzed may be walking. However, it should be appreciated that physical activity is not limited to walking.

Continuing from block 402 to 404 ("Filter Y-axis Signal"), the motion module 306 may filter the received y-axis accelerometer signal. In one example, the filtering may be performed by utilizing a Low Pass Filter with a cutoff at 12 Hz and a High Pass Filter with a cutoff at 1 Hz.

Continuing from block 404 to 406 ("Sample Filtered Signal"), the motion module may sample the filtered accelerometer signal. In one example, the filtered accelerometer signal may be received at a 500 Hz sampling rate.

Continuing from block 406 to 408 ("Average Each Sample"), the motion module 306 may for each sample, average the sample together with the 99 previous samples (i.e., the mean of 100 samples) and multiply by 5 to implement a digital filter utilized in digital signal processing applications. In one example, the digital filter may be a Finite Impulse Response (FIR) filter.

Continuing from block 408 to 410 ("Invert Filtered Signal"), the motion module 306 may invert the filtered signal (e.g., FIR filtered signal) to facilitate using a detected physical activity. In this example, the physical activity may be walking, in which case, the motion module 306 may invert the FIR filtered signal to facilitate using a step detector.

Continuing from block 410 to 412 ("Process Inverted Signal"), the motion module 306 may process the inverted signal utilizing the step detector to count the number of steps.

The motion module may utilize the determined intensity to facilitate determination of a trend in the intensity of the physical activity. The motion module 306 may be configured to facilitate analysis of the trend in the intensity of the physical activity may be analyzed by the motion module 306, which may be utilized to determine one or more wellness parameters of the person. Additionally, the motion module 306 may be configured to facilitate determination of a pattern of the physical activity, which may be utilized to measure one or more wellness parameter of the person.

Figure 5:
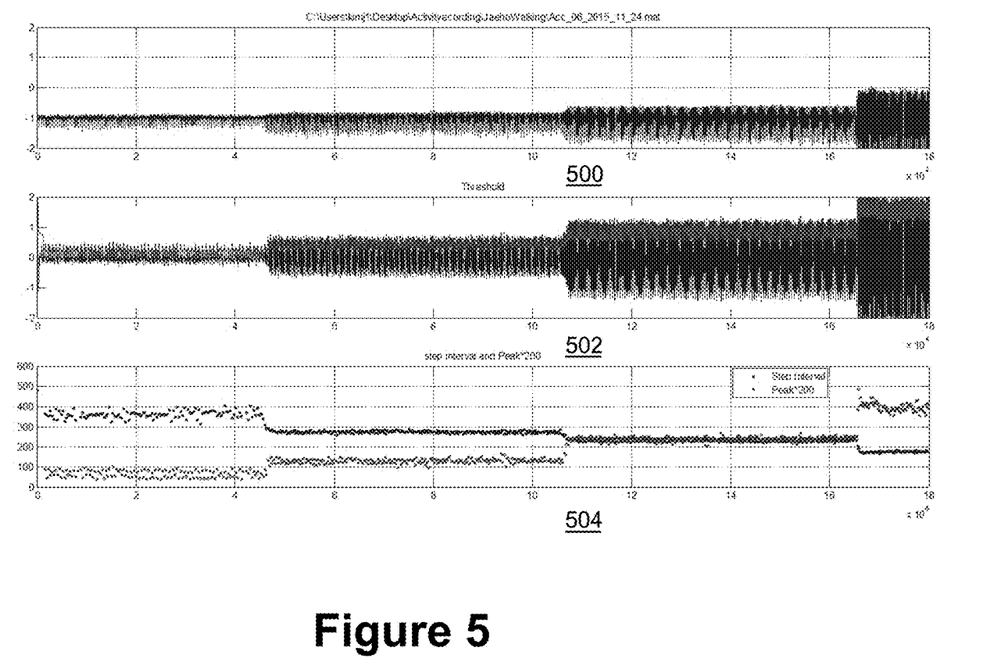
FIG. 5 illustrates an implementation of operational flow for detection of physical activity and its intensity, in accordance with various embodiments.

FIG. 5 illustrates an implementation of operational flow for detection of physical activity and its intensity, in accordance with various embodiments. In FIG. 5, the operational flow 400 (shown in FIG. 4) for detection of physical activity and its intensity as described with respect to FIG. 4 may be tested. As shown in FIG. 5, a chart 500 includes data related to a physical activity of walking. The chart 500 starts at a slower speed and gradually at a higher speed of walking. Application of the operational flow 400 on the data shown in the chart 500 show that the step intervals may be detected substantially reliably at a slower speed and a higher speed. A chart 502 illustrates a threshold for the step intervals detected. The chart 504 shows the result. In this example, the step intervals may be in samples with a sampling rate at 500 Hz. Accordingly, the typical step intervals may be between 300 ms and 1000 ms.

Figure 6:
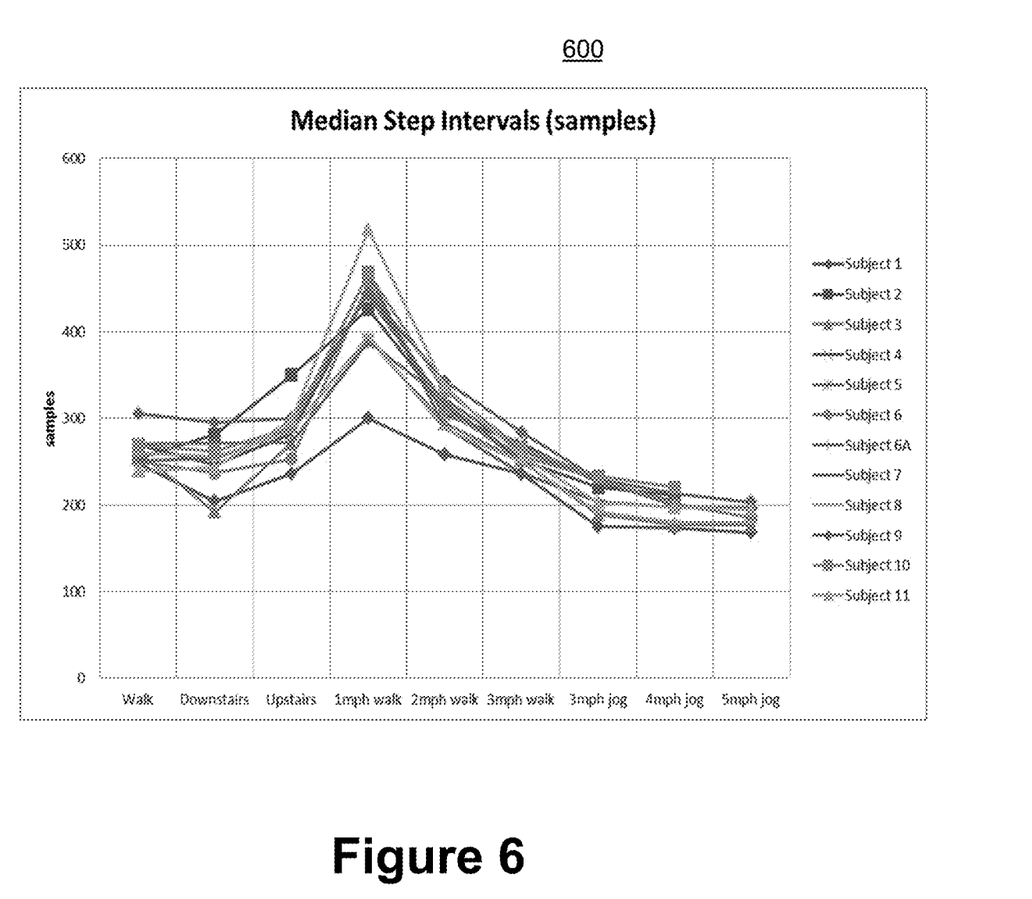
FIG. 6 illustrate a chart related to step/stride intervals (speed) for physical activities, in accordance with various embodiments.

FIG. 6 illustrate a chart related to step/stride intervals (speed) for physical activities, in accordance with various embodiments. In FIG. 6, a chart 600 illustrates step/stride intervals (speed) for different activities, by different subjects, obtained utilizing an embodiment of the step counter described herein. The chart 600 illustrating the step/stride intervals (speed) may be utilized to assess and/or promote health/wellness of a person, in accordance with various embodiments. For example, determine a trend in the intensity of the physical activity and/or a pattern of the physical activity, both of which may be utilized to measure one or more wellness parameter of the person.

Figure 7:
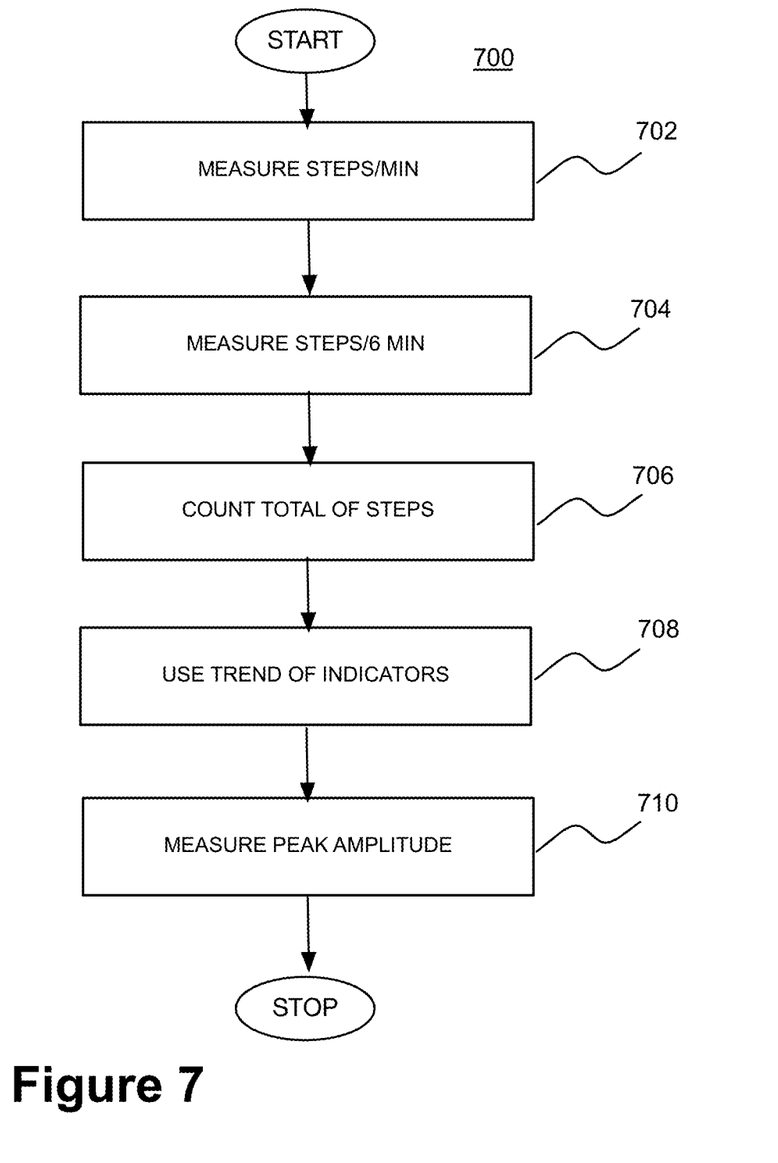
FIG. 7 illustrates an operational flow for one or more health/wellness indicators and for recommending activities, in accordance with at least some embodiments described herein.

FIG. 7 illustrates an operational flow for one or more health/wellness indicators and for recommending activities, in accordance with at least some embodiments described herein. In some portions of the descriptions, illustrative implementations of the method may be described with reference to a WCD depicted in FIGS. 1 and 2 and system for detecting motion and intensity of physical activity depicted in FIG. 3. Additionally, the methods and implementation of the operational flow may utilize methodologies described in in US Pat. App. Pub. No. US20190321648A1 filed Apr. 10, 2019 entitled "SUBSTANTIALLY-MEDIAN-BASED DETERMINATION OF LONG-TERM HEART RATES FROM ECG DATA OF WEARABLE CARDIO-VERTER DEFIBRILLATOR (WCD) SYSTEM" ("648 app"), which is incorporated herein in its entirety for all purposes.

FIG. 7 may employ block diagrams to illustrate the example methods detailed therein. These block diagrams may set out various functional blocks or actions that may be described as processing steps, functional operations, events and/or acts, etc., and may be performed by hardware, software, and/or firmware. Numerous alternatives to the functional blocks detailed may be practiced in various implementations. For example, intervening actions not shown in the figures and/or additional actions not shown in the figures may be employed and/or some of the actions shown in the figures may be eliminated. In some examples, the actions shown in one figure may be operated using techniques discussed with respect to another figure. Additionally, in some examples, the actions shown in these figures may be operated using parallel processing techniques. The above described, and other not described, rearrangements, substitutions, changes, modifications, etc., may be made without departing from the scope of claimed subject matter.

In order to describe the claimed subject matter, the example physical activity described may be a physical activity such as, but not limited to, walking.

In some examples, operational flow 700 may be employed as part of motion module 306 (shown in FIG. 3). Beginning at block 702 ("Measure Steps/min"), the motion module 306 may measure the steps/minute. The total minutes with steps/min>threshold (for example 90 steps/min) may be measured. Multiple thresholds may be utilized. For example, the total minutes with steps/min>70, the total minutes with steps/min>80, the total minutes with steps/min>90, the total minutes with steps/min>100, the total minutes with steps/min>110, the total minutes with steps/min>120, and so forth.

Continuing from block 702 to 704 ("Measure Steps/6 min"), the motion module 306 may measure the steps/6 minutes. That is, a peak number of steps/6 min may be recorded daily.

Continuing from block 704 to 706 ("Count Total of Steps"), the motion module may count a daily total of steps.

Continuing from block 706 to 708 ("Use Trend of Indicators"), the motion module 306 may use a trend of the indicators for relative change of health indicators for each person. For example, an increase of the daily total steps combined with an increase in the steps/6 min may be an indication that the person is getting healthier. Conversely, if the daily total steps or the steps/6 min shows a decreasing trend, a health indicator of the subject may be worsening, and a warning message may be provided and/or transmitted as previously described.

Continuing from block 708 to 710 ("Measure Peak Amplitude"), the motion module 306 may measure a peak amplitude along with the steps, where the peak amplitude may be a filtered Y-axis accelerometer signal peak amplitude.

As a result, the motion module 306 may determine a trend in the physical activity, which may be utilized to determine one or more wellness parameters of the person. Additionally, the motion module 306 may be configured to facilitate determination of a pattern of the physical activity, which may also be utilized to measure one or more wellness parameter of the person.

In general, the operational flow described with respect to FIG. 4, FIG. 7, and elsewhere herein may be implemented as a computer program product, executable on any suitable computing system, or the like. For example, a computer program product for determining intensity of physical activity may be provided.

Figure 8:
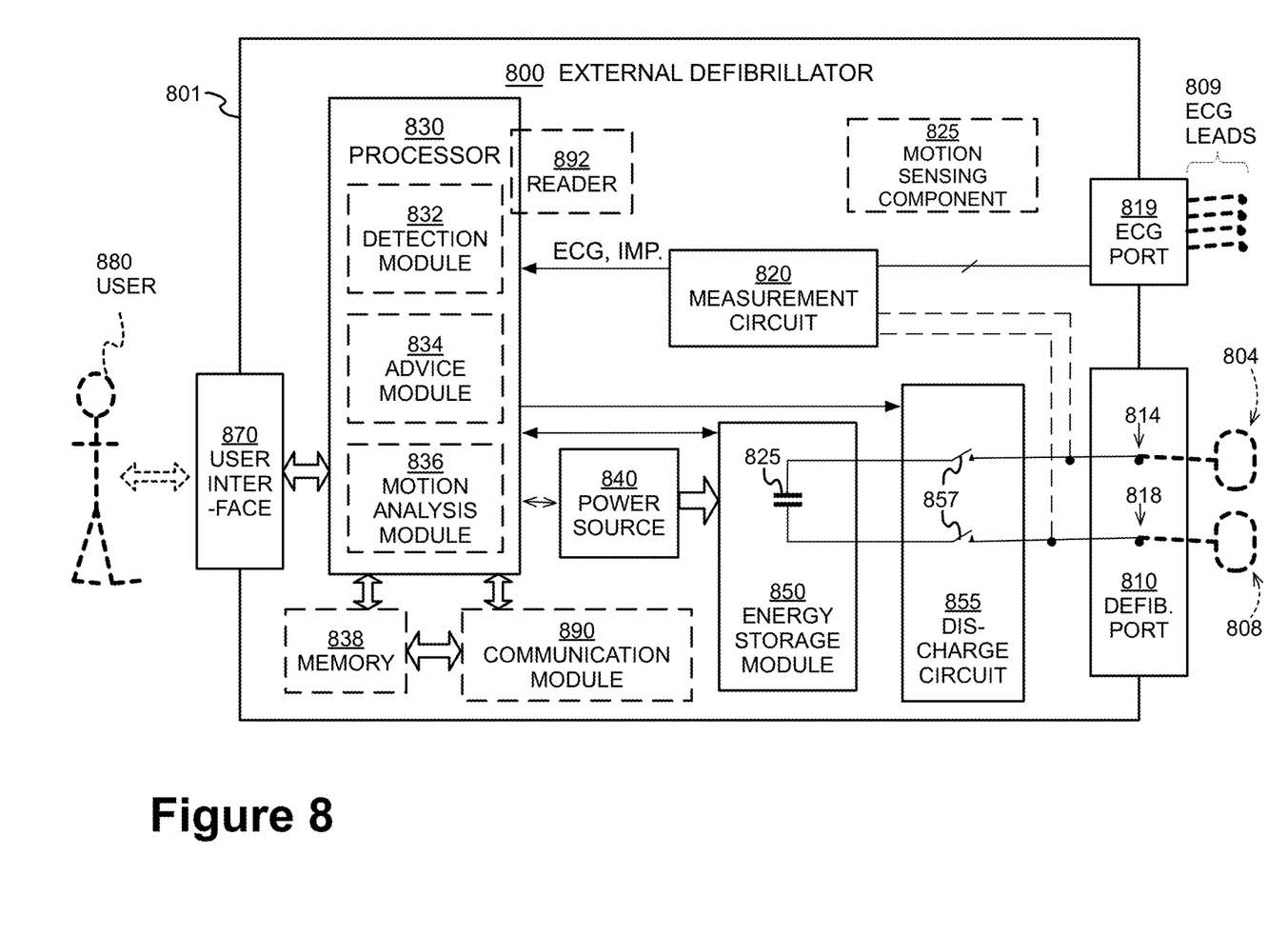
FIG. 8 is a block diagram illustrating components of reconfigurable medical device, in accordance with various embodiments.

FIG. 8 is a block diagram illustrating components of reconfigurable medical device, in accordance with various embodiments. These components may be, for example, components of medical device such as, but not limited to, a WCD 100 and 200 (shown in FIGS. 1 and 2).

The defibrillator device 800 may be some of the above examples of a one or more modules for the medical device intended for use by a user 880 (e.g., a wearer, a person, a patient, etc.). The defibrillator device 800 may typically include a defibrillation port 810, such as a socket in housing 801. The defibrillation port 810 may include nodes 814 and 818. One or more electrodes 804 and 808, which may be removably plugged into the defibrillation port 810, so as to make electrical contact with nodes 814 and 818, respectively. It may also be possible that the electrodes 804 and 808 may be connected continuously to the defibrillation port 810, etc. Either way, the defibrillation port 810 may be used for guiding via the electrodes 804 and 808 to a person 804 an electrical charge that may have been stored in the defibrillator device 700, as described herein.

The defibrillator device 800 may also have an ECG port 819 in the housing 801, for receiving ECG cables 809. The ECG cables 809 may facilitate sensing of an ECG signal (e.g., a 12-lead signal or from a different number of lead signals). Moreover, a defibrillator-monitor could have additional ports (not shown) making the defibrillator device 800 more reconfigurable, and a motion sensing component 825 may be configured to motion of a physical activity and may include one or more motion sensors as described herein. In some examples, there may be additional components configured to filter the ECG signal (e.g., application of at least one filter to the signal to help facilitate removal of artifacts such as, but not limited to, chest compression due to chest compressions being delivered to the person).

The defibrillator 800 also may include a measurement circuit 820. The measurement circuit 820 may receive physiological signals from the ECG port 819, and also from other ports, if provided. The circuit 820 may render detected physiological signals and their corresponding information. The information may be in the form of data, or other signals, etc.

The measurement circuit 820 may obtain physiological signals through the nodes 814 and 818, when the electrodes 804 and 808 are attached to the person. In these cases, a person's ECG signal may be detected as a voltage difference between the electrodes 804 and 808. Additionally, the impedance between the electrodes 804 and 808 may be detected, among other things, whether the electrodes 804 and 808 have been inadvertently disconnected from the person.

The defibrillator 800 may also include a processor 830. The processor 830 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 830 may include a number of modules. One example module may be a detection module 832, which may detect outputs from the measurement circuit 820. The detection module 832 may include a VF detector. Accordingly, the person's detected ECG may be utilized to help determine whether the person is experiencing ventricular fibrillation (VF).

In another example module may be an advice module 834, which may provide advice based, at least in part, on outputs of detection module 832. The advice module 834 may include an algorithm such as, but not limited to, Shock Advisory Algorithm, implement decision rules, and so on. For example, the advice may be to shock, to not shock, to administer other forms of therapy, and so on. If the advice is to shock, some defibrillator examples may report the advice to the user, and prompt them to do it. In other examples, the defibrillator device may execute the advice by administering the shock. If the advice is to administer CPR, the defibrillator 800 may further issue prompts for administrating CPR, and so forth.

The processor 830 may include additional modules, such as motion analysis module 836 for various motion related functions described herein. Additionally, if other motion sensing component 825 is provided, it may be operated in part by processor 830, etc.

In an example, the defibrillator device 800 may include a memory 838, which may work together with the processor 830. The memory 838 may be implemented in a wide variety of manners. For example, the memory 838 may be implemented such as, but not limited to, nonvolatile memories (NVM), read-only memories (ROM), random access memories (RAM), and so forth or any combination thereof. The memory 838 may can include programs for the processor 830, and so on. The programs may include operational programs execution by the processor 830 and may also include protocols and methodologies that decisions may be made by advice module 834. Additionally, the memory 838 may store various prompts for the user 880, etc. Moreover, the memory 838 may store a wide variety of information (i.e., data) such as, but not limited to information regarding the person.

The defibrillator 800 may also include a power source 840. In order to facilitate portability of defibrillator device 800, the power source 840 may include a battery type device. A battery type device may be implemented as a battery pack, which may be rechargeable or not be rechargeable. At times, a combination of rechargeable and non-rechargeable battery packs may be utilized. Additionally, the power source may be configured to be modified to accommodate the power level demands (e.g., monitoring mode without therapy or vice versa). Examples of power source 840 may include AC power override, where AC power may be available, and so on. In some examples, the processor 830 may control the power source 840.

Additionally, the defibrillator device 800 may include a configurable energy storage module 850. The configurable energy storage module 850 may be configured to store some electrical energy (e.g., when preparing for sudden discharge to administer a shock). The configurable energy storage module 850 may be charged from the power source 740 to an appropriate level of energy, as may be controlled by the processor 830. In some implementations, the configurable energy storage module 850 may include one or more capacitors 852, and the like.

The defibrillator 800 may include a discharge circuit 855. The discharge circuit 855 may be controlled to facilitate discharging of the energy stored in energy storage module 850 to the nodes 814 and 818, and also to electrodes 804 and 808. The discharge circuit 855 may include one or more switches 857. The one or more switches 857 may be configured in a number of manners such as, but not limited to, an H-bridge, and so forth.

The defibrillator device 800 may further include a user interface 870 for the user 880. The user interface 870 may be implemented in a variety of manners. For example, the user interface 870 may include a display screen capable of displaying what is detected and measured, provide visual feedback to the user 880 for their resuscitation attempts, and so forth. The user interface 870 may also include an audio output such as, but not limited to, a speaker to issue audio prompts, etc. The user interface 870 may additionally include various control devices such as, but not limited to, pushbuttons, touch display, and so forth. Additionally, the discharge circuit 855 may be controlled by the processor 830 or directly by the user 880 via the user interface 870, and so forth.

Additionally, the defibrillator device 800 may include other components. For example, a communication module 890 may be provided for communicating with other machines and/or the electrodes. Such communication may be performed wirelessly, or via wire, or by infrared communication, and so forth. Accordingly, information may be communicated, such as person data, incident information, therapy attempted, CPR performance, ECG information, and so forth.

The above described components may be configured and reconfigured, in accordance with various embodiments. For example, monitoring mode or monitoring and therapy mode.

It should be appreciated after review of this disclosure that it is contemplated within the scope and spirit of the present disclosure that the claimed subject matter may include a wide variety of healthcare devices. Accordingly, the claimed subject matter is not limited in these respects.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter is not limited to the particular examples disclosed, but that such claimed subject matter also may include all implementations falling within the scope of the appended claims, and equivalents thereof.

What is claimed:

1. A wearable cardioverter defibrillator (WCD) system comprising:
   a support structure, the support structure configured to be worn by a person;
   a motion sensor coupled to the support structure; and
   a motion analysis module (MAM) communicatively coupled with the motion sensor, the MAM configured to:
      receive data from the motion sensor,
      determine if the person is walking from the received data,
      responsive to the determination that the person is walking, determine a number of steps,
      calculate, based on a determined number of steps, a steps/minute value, a steps/6 minutes value, and a total daily steps value,
      determine a trend based at least in part on the steps/minute value, the steps/6 minutes value, and the total daily steps value, wherein the trend is indicative of a change in a health condition of the person,
      calculate a wellness parameter based on the trend, and
      output a recommendation for the person based on the wellness parameter, wherein the recommendation includes at least one of a recommended activity or activity level.

2. The WCD system of claim 1 further comprising a display device communicatively coupled to the MAM, the display device configured to receive and display the trend.

3. The WCD system of claim 1, wherein the motion sensor comprises an accelerometer.

4. The WCD system of claim 3, wherein the accelerometer is positioned to be proximate to a back of the person wearing the WCD.

5. The WCD system of claim 3, wherein the accelerometer comprises a 3-axis accelerometer configured to measure acceleration and/or orientation relative to gravity along 3 orthogonal axes, the 3 orthogonal axes comprising an X axis, a Y axis, and a Z axis.

6. The WCD system of claim 5, wherein the Y axis substantially corresponds to an up and down acceleration of the person wearing the WCD.

7. The WCD system of claim 1, wherein the MAM is further configured to filter an accelerometer signal, wherein to implement the filter the MAM is configured to:
   receive a y-axis accelerometer signal from the motion sensor; sample the y-axis accelerometer signal;
   average the sample together with a predetermined number of previous samples;
   multiply by a predetermined multiplier resulting in a filtered signal;
   invert the filtered signal; and
   output the inverted filtered signal.

8. The WCD system of claim 1, wherein for each set of one or more additional sets of determined numbers of steps each different from the determined number of steps, the MAM is further configured to determine:
   a steps/minute value; and
   a steps/6 minutes value.

9. The WCD of claim 8, wherein the MAM is further configured to determine, based on at least the determined number of steps and the additional sets of determined number of steps, an average walking intensity in a day, and/or a peak walking intensity in a day.

10. A method for determining a walking intensity of a person wearing a wearable cardioverter defibrillator (WCD), the method comprising:
    receiving a y-axis accelerometer signal from a motion sensor;
    determining whether the person is walking at least in part from the received y-axis accelerometer signal;
    responsive to the determination that the person is walking, determining a number of steps;
    calculating, based on a determined number of steps, a steps/minute value, a steps/6 minutes value, and a total daily steps value;
    determining a trend based at least in part on the steps/minute value, the steps/6 minutes value, and the total daily steps value, wherein the trend is indicative of a change in a health condition of the person,
    calculating a wellness parameter based on trend, and
    outputting a recommendation for the person based on the wellness parameter, wherein the recommendation includes at least one of a recommended activity or activity level.

11. The method of claim 10, wherein the motion sensor is positioned by the WCD to be proximate to a back of the person.

12. The method of claim 10, further comprising determining, for additional sets of determined numbers of steps each different from the determined number of steps, a steps/minute value and a steps/6 minutes value.

13. The method of claim 12, further comprising determining, based on at least the determined number of steps and the additional sets of determined number of steps, an average walking intensity in a day, and/or a peak walking intensity in a day.

14. The method of claim 10 wherein outputting the trend comprises communicating the trend to a display device.

15. The method of claim 10 further comprising filtering the received y-axis accelerometer signal, wherein the filtering comprises:
    sampling the received y-axis accelerometer signal;
    averaging a predetermined number of samples provided by the sampling;
    multiplying by a predetermined multiplier the average, resulting in a filtered signal;
    inverting the filtered signal; and
    outputting the inverted filtered signal.

16. The method of claim 10 further comprising determining whether the trend is decreasing.

17. The method of claim 10 further comprising determining whether the trend is increasing.

18. A method for monitoring a health condition of a person wearing a wearable cardioverter defibrillator (WCD), the method comprising:
    measuring a steps/minute taken by the person based, at least in part, on a detected motion of the WCD;
    measuring a steps/6 minutes taken by the person based, at least in part, on the detected motion of the WCD;
    counting a daily total of steps taken by the person based, at least in part, on the detected motion of the WCD;
    determining a trend based at least in part on the steps/minute, the steps/6 minutes, and the total daily steps, wherein the trend is indicative of a change in the health condition of the person,
    calculating a wellness parameter based on the trend; and
    outputting a recommendation for the person based on the wellness parameter, wherein the recommendation includes at least one of a recommended activity or activity level.

19. The method of claim 18, wherein determining the trend comprises measuring a total time of steps/min exceeding a predetermined threshold.

20. The method of claim 18, wherein measuring the steps/6 minutes comprises a peak steps/6 minutes and recording the number of the peak steps/6 minutes.

21. The method of claim 18 further comprising measuring a peak amplitude of the steps.

22. The method of claim 18 further comprising determining whether the trend is decreasing.

23. The method of claim 18 further comprising determining whether the trend is increasing.

* * * * *